United States Patent [19]

Kuntz et al.

[11] Patent Number: 5,753,026
[45] Date of Patent: May 19, 1998

[54] PROCESS FOR THE PREPARATION OF INCLUSION PIGMENTS

[75] Inventors: Mathias Kuntz, Ober Beerback; Hubert Linne, Otzberg; Joachim Weitzel, Darmstadt; Dieter Heinz, Heppenheim, all of Germany; Rodney Riddle, Dorset, United Kingdom

[73] Assignee: Merck Patent Gesellschaft mit Beschrankter Haftung, Darmstadt, Germany

[21] Appl. No.: 734,635

[22] Filed: Oct. 21, 1996

[30] Foreign Application Priority Data

Oct. 20, 1995 [DE] Germany ............... 195 39 116.0

[51] Int. Cl.$^6$ ............... C09C 1/00; C09C 1/28; C09C 1/40
[52] U.S. Cl. ............... 106/450; 106/401; 106/481; 106/482; 423/592; 423/593; 423/608; 423/618; 423/625
[58] Field of Search ............... 106/401, 450, 106/481, 482; 501/1, 94; 423/592, 593, 608, 618, 625; 424/401

[56] References Cited

U.S. PATENT DOCUMENTS

| | | |
|---|---|---|
| 5,149,369 | 9/1992 | Eberts et al. |
| 5,177,055 | 1/1993 | Kinsman et al. ............... 501/94 |
| 5,194,089 | 3/1993 | Speer et al. |
| 5,252,125 | 10/1993 | Speer et al. ............... 106/450 |
| 5,268,337 | 12/1993 | Katz et al. ............... 501/94 |
| 5,614,472 | 3/1997 | Riddle et al. ............... 505/425 |

FOREIGN PATENT DOCUMENTS 473 621  10/1990  European Pat. Off. .

OTHER PUBLICATIONS

Abstract of EP 473,621 Oct. 5, 1990.

Primary Examiner—Michael Marcheschi
Attorney, Agent, or Firm—Millen, White, Zelano, & Branigan, P.C.

[57] ABSTRACT

Reaction spray process for preparing inclusion pigments by suspending the pigment to be encapsulated in an aqueous solution or suspension of a precursor of the inclusion material, spraying the suspension, with or without the addition of nitric acid and fuel, in a tubular reactor heated at from 850° to 1100° C., separating the inclusion pigment from the product stream and, if desired post-calcining the pigment at a temperature of at least 816° C.

19 Claims, No Drawings

PROCESS FOR THE PREPARATION OF INCLUSION PIGMENTS

The invention relates to a process for the preparation of inclusion pigments by a spray pyrolysis process.

BACKGROUND OF THE INVENTION

Processes for the preparation of inclusion pigments are known. They have been developed in order to enable the preparation of weather-stable and temperature-stable pigments. For example, for glazes in the decorative firing of ceramics or for porcelain, pigments are required which are stable even up to temperatures of 1500° C.

Pearl luster pigments are unsuitable as inglaze pigments for the decoration firing of ceramics since under the action of the network modifiers sodium and potassium and of flux assistants such as lead, boron or bismuth they break up almost completely even within short firing cycles. It is therefore necessary to render these pigments useable for the abovementioned application by means of an additional coating.

Furthermore, for some applications it is advantageous to have available pearl luster pigments coated with silicon dioxide. A coat of $SiO_2$ increases, for example, the stability to yellowing and the stability in aqueous coating systems.

DE 40 14 928 describes a process for the preparation of coated spinel color pigments, having a core comprising a colored spinel and a vitreous layer which at least partially coats this core and comprises a siliceous material, and said process entailing the sintering of a homogeneous powder mixture comprising the colored spinel, silicon dioxide and at least one mineralizer from the series consisting of the halides of alkali metals, alkaline earth metals and/or earth metals at from 900° to 1300° C. for from 0.5 to 5 hours and the wet or dry milling of the sintered product.

EP 498 686 describes a process for the preparation of a weather-resistant pearl luster pigment, in which a layer of cerium hydroxide is precipitated onto the pearl luster pigment. For this purpose, the pearl luster pigment (bismuth oxychloride) is dispersed in a cerium salt solution and, by altering the pH from 6.2 to 10, cerium hydroxide is deposited on the platelet-shaped pearl luster pigment.

These processes have the disadvantage that when the pigment is calcined the particles sinter together with one another and the product must be remilled. Such remilling, however, partly damages the coating again and leads to the desired aim being only partly achieved. Furthermore, it has been found that the complete inclusion of the pigments within the oxide or silicate coat material, for example $Zro_2$, $SnO_2$, $Al_2O_3$ or $ZrSiO_4$, is practically not possible by these processes.

EP 0 341 274 discloses a process for the preparation of multi-element metal oxide powders for use as precursors for the preparation of high temperature-superconducting ceramics by mixing metal salt solutions in the stoichiometric ratio which is required for the desired end product, spraying the homogeneous solution into a horizontal tubular furnace heated at a temperature of from 800° to 1100° C., conveying the spray mist along the principal axis of the furnace by means of hot air, and collecting the finely divided metal oxide powder by means of a filter.

DE 39 16 643 discloses a process for the preparation of ceramic oxide powders. This is a pyrolytic process for the preparation of ceramic oxide powders by burning corresponding aqueous solutions, containing metal nitrates, in the presence of elemental carbon or organic substances which act as fuel, the quantity of nitrate in solution being matched to the quantity of fuel such that the combustion is largely self-supporting after ignition means of the hot ignition source which has a temperature of at least 250° C. by a hot ignition source which has a temperature of at least 250° C., in the course of which combustion at least 75% of the nitrate oxygen contributes to the complete combustion of the fuel. Nitrate solution and fuel can be sprayed as a mixture or separately into the reaction chamber, where ignition of the mixture takes place by

SUMMARY OF THE INVENTION

An object of the invention is to provide a process with which complete coating of the pigment particles is achieved and agglomeration of the coated pigment particles is prevented.

Upon further study of the specification and appended claims, further objects and advantages of this invention will become apparent to those skilled in the art.

It has surprisingly now been found that when a spray pyrolysis process is used it is possible to prepare inclusion pigments of the desired quality, by suspending the pigment to be encapsulated in an aqueous solution or suspension of the inclusion material, spraying the suspension in a horizontal tubular furnace at from 850° to 1100° C., preferably from 850° to 900° C., conveying the spray mist along the principal axis of the furnace by means of hot air and collecting the inclusion pigment by means of appropriate devices, for example by means of a filter. Further details of this process are described more closely in EP 0 341 274. The process is also known under the name EDS (Evaporative Decompositions of Solutions). In accordance with a further embodiment of the process according to the invention, the inclusion pigments of the desired quality are also prepared by NPP processes, in which the pigment to be encapsulated is suspended in an aqueous solution or suspension of a precursor of the inclusion material, nitric acid and, if desired, fuel are added to the pigment suspension, the fuel and the pigment suspension, containing nitric acid, are sprayed, in a mixture or separately, into a reaction chamber where ignition takes place by a hot ignition source which has a temperature of at least 250° C., and the resulting inclusion pigment is collected in suitable devices, for example filters, collection chambers or cyclones, the quantity of nitric acid in the pigment suspension being matched to the quantity of fuel in such a way that combustion is largely self-supporting after ignition, at least 75% of the nitric acid contributing to the complete combustion of the fuel. Further details of this process are described in DE 39 16 643. This process is also known as the NPP (Nitrate Pyrolysis Plant) process.

Furthermore, inclusion pigments according to the invention can be prepared by a process using hydrogen/oxygen flame which is described in EP 681 989. The suspension is sprayed through a hydrogen/oxygen flame in such a way that a flame temperature of 800° to 1100° C. is maintained and a contact of the aerosols and the pigment generated during the process with carbon or carbon containing compounds or materials is strictly avoided.

Furthermore, it is a subject of the present invention that the inclusion pigments are used for pigmented paints, printing inks, plastics, cosmetics and glazes for ceramics and glasses. The inclusion pigments can be also used as mixtures with customary commercial pigments.

Subjects of the present invention are also paints, cosmetics, ceramics and glazes pigmented with a pigment according to the invention.

The inclusion material (coat material) used for the inclusion pigments comprises oxide or siliceous materials such as, for example, $ZrO_2$, $SnO_2$, $Al_2O_3$, $SiO_2$ or $ZrSiO_4$, with preference being given to $ZrSiO_4$ and $SiO_2$. Precursors of the coat materials are employed in the initial suspension. By precursors are meant water-soluble salts of the oxide-forming metals, for example zirconyl chloride or zirconyl nitrate, or sols, for example zirconium oxide sol or silicon dioxide sol. In the case of $ZrSiO_4$ as coat material it is necessary to employ a zirconium component (zirconyl nitrate or a zirconium oxide sol) and a siliceous component (silicate or silicon dioxide sol) as precursor.

Colorants such as metal salts or metal oxides may also be present in suspended or dissolved form in the initial suspension, whereby it is also possible to obtain colored coatings.

The suspension can, if desired, also comprise a mineralizer, for example lithium nitrate. The mineralizer is added to the pigment suspension in a concentration of from 5 to 50 mol % based on the coat material, for example $ZrSiO_4$.

The thickness of the coat is established as a function of the intended use of the inclusion pigment. For use in glazes, the pigments are preferably coated with a layer of zirconium silicate having a thickness of from 10 to 1000 nm. For the use of the pigments in aqueous coating systems, it is preferred to apply a silicon dioxide coat having a thickness in the range from 5 to 100 nm.

The pigments to be encapsulated may be inorganic and, in certain circumstances, organic pigments. Suitable pigments are spherical absorption pigments or else platelet-shaped interference pigments based on mica or other platelet-shaped substrates, for example talc, kaolin, or glass flakes and metal pigments.

Preferred platelet-shaped materials are mica and platelet-shaped pigments prepared in a accordance with the international application PCT/EP92/02351. These consist of a transparent, inorganic platelet-shaped matrix, preferably silicon dioxide. The matrix is prepared by solidifying a liquid precursor on a continuous belt. Additional constituents can be incorporated into this matrix.

The platelet-shaped materials typically have a thickness of from about 0.05 to 5 µm and, in particular, of from 0.2 to 2 µm. The extent in the two other dimensions is preferably from 1 to 250 µm and, in particular, from 5 to 60 µm. The ratio of the extent in the principal dimension to the thickness (aspect ratio) is more than 3 and preferably more than 5.

Furthermore it is also possible to encapsulate organic pigments, for example DPP red or methylene blue, by the process according to the invention, in order to protect them against chemical and mechanical attack.

The concentration of pigment in the initial suspension is between 1 and 50% by mass, preferably between 5 and 30% by mass. It depends on the desired thickness of the coat.

Suitable fuels for the NPP process of the invention are, primarily, gaseous hydrocarbons, aliphatic or aromatic hydrocarbons or aliphatic alcohols, coal dust or mixtures of these substances. However, the applicability is not restricted to the selection made primarily on economic grounds.

Gaseous hydrocarbons are preferably methane, propane, butane and mixtures thereof. Natural gas, which consists essentially of gaseous hydrocarbons, is a readily available and particularly economic fuel.

By aliphatic or aromatic hydrocarbons or aliphatic alcohols are meant in principle all appropriate common organic solvents such as, for example, pentane, hexane, benzene, toluene, xylene, methanol, ethanol and also hydrocarbon mixtures such as naphthas and heavy naphthas, diesel oil, etc. A suitable solid fuel is, above all, coal dust.

It is essential to the process according to the invention and to all of its embodiments that the fuels employed are all ignitable by a hot ignition source which has a temperature of at least 250° C.

The specific implementation of the process can be configured in different ways and adapted in an optimum manner to the prevailing material conditions, depending on the initial situation.

One variant consists in firstly intimately mixing the nitrate solution with the fuel and then feeding it as a mixture to the combustion. This variant is particularly suitable when liquid fuels are to be employed. However, coal dust can also be dispersed, together if desired with liquid fuels, with the solution and thus burned as a mixture. This method of mixture combustion is optimal if water-soluble or water-miscible fuels, for instance aliphatic alcohols, are employed.

Another variant comprises supplying nitrate solution and fuel separately and mixing them intimately only during combustion. This variant is to be preferred if the fuels are water-immiscible liquids, such as hydrocarbons. This method is optimal if gaseous hydrocarbons are employed as fuel. This is a particularly preferred embodiment of the process according to the invention.

Yet another variant consists in supplying both nitrate solution and fuel, as a mixture, and additional fuel, separately, to the combustion. This variant is particularly suitable when gaseous, liquid and, if desired, solid fuels are to be employed. This method can be managed favorably if about 10-20% by weight of the fuel employed is in solid form, 50-70% by weight is in liquid form and 20-30% by weight is in gaseous form.

In all of its variants, the process according to the invention can be carried out in installations or plants, such as are known in principle from conventional spray pyrolysis processes. Such installations and plants generally consist of a tubular reactor, which is constructed in principle from an inlet zone for the medium to be sprayed, a reaction zone, in which pyrolysis takes place, and an outlet zone, which opens into a device for separating off the reaction product. In this arrangement, the inlet zone usually consists of one or more nozzles through which the medium, under control if desired, is sprayed. The reaction zone is usually heated indirectly by a furnace or directly by the supply of hot combustion gases. Collection of the reaction product is usually effected by filters, collection chambers or one or more cyclones. The person skilled in the art is familiar with the corresponding plant and technical possibilities and is able to apply them without problems to the specific circumstances of the process according to the invention. The dimensioning of such a plant is dependent on the desired production capacity and the method of operation, that is to say whether partial or long-term continuous operation is intended.

In order to carry out the NPP process it is necessary for the solution/fuel mixture which is sprayed into the reactor or forms therein to be ignited, so that the reaction is established in the form of a self-supporting, complete combustion. For this purpose the mixture must come into contact with a hot ignition source which is at a temperature of at least 250° C. Suitable ignition sources are, for example, the appropriately externally heated tube walls of the reactor, or ignition sources installed separately in the reactor, such as glow plugs, spark plugs, a pilot flame, electrically heated heating wires or incandescent gratings. Ignition by means of a pilot burner operated with gas and air proves particularly expedient and effective.

After the reaction has been initiated, i.e. after ignition of the reaction mixture and development of a constant combustion reaction with continuous supply of the reaction mixture, the temperatures rapidly established in the reactor are so high, typically above 1000° C., that further operation of the ignition source can normally be dispensed with. However, it may be worthwhile, merely for operational safety, for instance in more critical individual cases, to continue to operate the ignition source, preferably in the form of a sustaining flame.

For the particularly preferred variant of the NPP process according to the invention, that is to say the combustion of the nitrate solution in the presence of gaseous hydrocarbons as fuel, it is expedient to design the gas supply from the outset in the form of a gas burner, into the flame zone of which the nitrate solution is sprayed. To start up the operation, provision is first made for ignition and combustion of the fuel gas by an appropriate supply of air, and, after switching on the spray injection of solution, the quantities of gas, air and solution supplied are regulated such that the combustion of the fuel gas takes place essentially by means of the pyrolysis of the nitrate solution. This regulation can, for example, advantageously be achieved with the aid of a lambda probe which is installed in the reactor and measures the partial pressure of oxygen in the reaction off-gas, on the basis of which pressure it is possible to establish an essentially stoichiometric combustion.

A particularly suitable reactor for the implementation of the NPP process comprises a horizontal tube which is 300 cm long and has an internal diameter of 20 cm. A gas burner head is located at the top end, the nozzles of said burner head being supplied with propane/butane mixture and air, with electrical ignition. The pigment suspension is sprayed into the flame cone by means of a nozzle arranged centrally in the burner head.

In the rear section of the reactor a lambda probe is installed with the aid of which the reactor atmosphere can be adjusted by way of the regulation of the gas/air supply. The inclusion pigment is collected in downstream chamber filters.

A reactor which is suitable for the implementation of the process according to the invention is a spray calcining reactor as described in more detail in EP 0 341 274. This is a horizontal tubular reactor which is heated at from 850° to 1100° C. At one end of the tube is a spray head which is supplied with the pigment suspension and hot air under a pressure of 0.34–0.52 bar.

At the other end of the tube is a collecting device, for example a filter, whose purpose is to remove the inclusion pigment formed from the gas stream.

If appropriate, post-calcination of the resulting inclusion pigment may be necessary. When zirconium silicate is used as inclusion material a temperature of 816° C. is necessary for complete phase conversion. If the pigment particles in the reactor are not heated to this temperature, subsequent calcining at at least 816° C. is necessary in order to bring about complete phase conversion into zirconium silicate.

The process according to the invention has the great advantage that the inclusion pigments obtained need no longer be milled. The desired particle size and its distribution can be established by an appropriately chosen fraction of the pigment employed. The pigments are completed coated. This applies, surprisingly, even to platelet-shaped pigments, which could not have been expected by the person skilled in the art.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German Application No. 195 39 116.0, filed Oct. 20, 1995, are hereby incorporated by reference.

The examples which follow are intended to illustrate the invention without limiting it.

EXAMPLES

Example 1

500 g of IRIODIN® 306 pigment are suspended in a mixture of 471 g of sodium silicate and 4.6 l of water. The resulting suspension, which has a volume of 5 l, is stirred continuously during spraying in a spray calcination reactor. To this end it is pumped at a rate of 1 l/h through a dual-substance nozzle and atomized with compressed air at 2 bar. The aerosol obtained is passed through a tubular reactor heated at 850°–900° C. After passing through the reaction zone, the product stream is led into an evacuated chamber and the product is deposited on a sintered steel filter. Over the course of 3 hours, 25 g of product are obtained from 2 l of pigment suspension.

The inclusion pigment has a 100 nm thick coat of silicon dioxide. The thickness of the coat was determined optically in a scanning electron microscope, with coated pigment particles being embedded in lacquer and broken.

Example 2

100 g of IRIODIN® 306 pigment are suspended in a mixture of 27.5 g of LUDOX® (a siliceous material suitable for coating, from DuPont) and 2 l of water. The resulting suspension, which has a volume of 2.5 l, is stirred continuously in order to prevent settling of the pigment. The suspension is pumped at a rate of 1 l/h through a dual-substance nozzle and atomized with compressed air at 1 bar. The aerosol obtained is passed through a tubular reactor heated at 850°–900° C. After passing through the reaction zone, the product stream is led into an evacuated chamber and the inclusion pigment is deposited on a sintered steel filter. Over the course of 4 hours, 34 g of product are obtained.

The thickness of the silicon dioxide coat is 25 nm.

Example 3

100 g of IRIODIN® 306 pigment are suspended in a mixture of 10.3 g of LUDOX®, 15.7 g of $ZrO(NO_3)_2$, 28.5 g of $LiNO_3 \cdot 3H_2O$ and 2 l of water. The resulting suspension which has a volume of 2.5 l, is stirred continuously in order to prevent settling of the pigment. The suspension is pumped at a rate of 1 l/h through a dual-substance nozzle and atomized with compressed air at 1 bar. The aerosol obtained is passed through a tubular reactor heated at 850°–900° C. After passing through the reaction zone, the product stream is led into an evacuated chamber and the inclusion pigment is deposited on a sintered steel filter. Over the course of 5 hours, 12 g of product are obtained, which is subsequently calcined in a tube furnace at 816° C. for 30 minutes. XRD analysis of the calcined product shows the presence of a zirconium silicate phase. The thickness of the zirconium silicate coat is 25 nm.

Example 4

50 g of IRIODIN® 306 pigment are suspended in a mixture of 206.3 g of LUDOX®, 380.2 g of ZrO(NO$_3$)$_2$, 109.5 g of LiNO$_3$·3H$_2$O and 2 l of water. The resulting suspension, which has a volume of 2.5 l, is stirred continuously in order to prevent settling of the pigment. The suspension is pumped at a rate of 1 l/h through a dual-substance nozzle and atomized with compressed air at 1 bar. The aerosol obtained is passed through a tubular reactor heated at 850°–900° C. After passing through the reaction zone, the product stream is led into an evacuated chamber and the inclusion pigment is deposited on a sintered steel filter. Over the course of 6 hours, 126 g of product are obtained, which is subsequently calcined in a tube furnace at 816° C. for 30 minutes.

XRD analysis of the calcined product shows the presence of a zirconium silicate phase. The thickness of the zirconium silicate coat is 400 nm.

Example 5

10 g of IRIODIN® 306 pigment are suspended in a mixture of 41.2 kg of LUDOX®, 76.04 kg of zirconyl nitrate solution, 21.9 kg of lithium nitrate and 400 kg of 65% nitric acid and the suspension obtained is stirred continuously. The suspension is sprayed at a rate of 15–30 kg/h into the flame cone of an NPP reactor. Prior to spray injection into the reactor, acetic acid is metered in via a static mixer. A total of 202 kg of acetic acid is required. In this context, a slight excess of reducing agent (acetic acid) relative to the quantity of nitrate employed was established. The residual amount of reducing agent required for stoichiometric combustion was achieved by way of the flame setting and was monitored by means of a λ probe at the end of the tubular reactor. The process was monitored and controlled by a thermocouple and the temperature in the reactor was maintained at from 1000° to 1300° C.

The product obtained was completely coated and a had a zirconium silicate phase.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope

What is claimed is:

1. A pyrolytic process for the preparation of a pigment completely coated by an inclusion material which comprises spraying a pigment suspension, comprising the pigment suspended in either an aqueous solution or suspension of a precursor of the inclusion material, into a horizontal tubular furnace heated at from 800° to 1100° C. while conveying the spray along the furnace by means of hot air.

2. A pyrolytic process according to claim 1, wherein the pigment suspension is sprayed through a hydrogen/oxygen flame for ignition, in such a way that a flame temperature of 800° to 1100° C. is maintained, whereby any contact of aerosols and the pigment generated during the process with carbon or carbon containing compounds or materials is avoided.

3. The process according to claim 1, wherein the pigment completely coated within the inclusion material is subsequently calcined at a temperature of at least 816° C. for 10 to 50 minutes.

4. The process according to claim 3, wherein the precursor of the inclusion material is a water-soluble salt or oxide hydrate sol of zirconium, silicon, tin or aluminum.

5. A pyrolytic process according to claim 1, wherein the pigment suspension further comprises nitric acid, and the process further comprises spraying a fuel into the furnace either separately or in a mixture with the pigment suspension and igniting the fuel by means of an ignition source having a temperature of at least 250° C., wherein the quantity of nitric acid and fuel are supplied in amounts such that combustion of the fuel takes place essentially by means of pyrolysis of the nitric acid and at least 75% by weight of oxygen necessary for combustion is supplied by the nitric acid.

6. The process according to claim 5, wherein the fuel is a gaseous hydrocarbon, aliphatic or aromatic hydrocarbon, aliphatic carboxylic acid, aliphatic alcohol, coal dust or a mixture thereof.

7. A method for pigmenting a paint, printing ink, plastic, cosmetic or glaze comprising adding a pigment prepared according to claim 1.

8. The method of claim 7, further comprising adding an colorant.

9. The process of claim 1, wherein the furnace is heated to 850° to 900° C.

10. The process of claim 1, wherein the pigment suspension further comprises a mineralizer in the amount of 5 to 50 mol % based on the inclusion material.

11. The process of claim 10, wherein the mineralizer is lithium nitrate or ZrSiO$_4$.

12. The process of claim 1, wherein the inclusion material coating has a thickness of is from 5 to 1000 nm.

13. The process of claim 1, wherein the pigment is a spherical absorption pigment, a platelet-shaped interference pigment or an organic pigment.

14. The process of claim 1, wherein the pigment is a platelet-shaped interference pigment.

15. The process of claim 1, wherein the concentration of pigment in the pigment suspension is 1 to 50% by mass.

16. The process of claim 1, wherein the inclusion material is ZrO$_2$, SnO$_2$, Al$_2$O$_3$, SiO$_2$ or ZrSiO$_4$.

17. The process of claim 1, wherein the inclusion material is SiO$_2$ or ZrSiO$_4$.

18. A method for pigmenting a paint, printing ink, plastic, cosmetic or glaze comprising adding a pigment prepared according to claim 13.

19. A method for pigmenting a paint, printing ink, plastic, cosmetic or glaze comprising adding a pigment prepared according to claim 14.

* * * * *